(12) United States Patent
Rella et al.

(10) Patent No.: US 9,310,346 B1
(45) Date of Patent: Apr. 12, 2016

(54) METHODS FOR RAPID GAS SAMPLING WITH HIGH HORIZONTAL SPATIAL RESOLUTION IN A MANNER SUITABLE FOR SUBSEQUENT CONSTITUENT GAS ANALYSIS

(71) Applicant: Picarro, Inc., Santa Clara, CA (US)

(72) Inventors: Chris W. Rella, Sunnyvale, CA (US); Pieter P. Tans, Coulder, CO (US)

(73) Assignee: Picarro, Inc., Santa Clara, CA (US)

( * ) Notice: Subject to any disclaimer, the term of this patent is extended or adjusted under 35 U.S.C. 154(b) by 447 days.

(21) Appl. No.: 13/715,026

(22) Filed: Dec. 14, 2012

Related U.S. Application Data

(60) Provisional application No. 61/630,770, filed on Dec. 15, 2011.

(51) Int. Cl.
*G01N 7/00* (2006.01)
*G01N 33/00* (2006.01)

(52) U.S. Cl.
CPC .................................. *G01N 33/0009* (2013.01)

(58) Field of Classification Search
CPC .. G01N 33/0009; G01N 33/0004; G01N 1/22
USPC ........................................................... 73/23.2
See application file for complete search history.

(56) References Cited

U.S. PATENT DOCUMENTS

| | | | |
|---|---|---|---|
| 3,547,587 A * | 12/1970 | Innes | 436/134 |
| 7,597,014 B2 | 10/2009 | Tans | |
| 8,597,580 B2 * | 12/2013 | von Bahr et al. | 422/84 |
| 2007/0023641 A1 * | 2/2007 | Weitz | 250/288 |
| 2008/0268544 A1 * | 10/2008 | Whalen | 436/2 |

* cited by examiner

*Primary Examiner* — Hezron E Williams
*Assistant Examiner* — Rodney T Frank
(74) *Attorney, Agent, or Firm* — Lumen Patent Firm

(57) ABSTRACT

A gas sample storage chamber is used to continuously acquire a gas sample. After the sample has been acquired, the stored gas in the chamber can be analyzed. This analysis can provide a time history of the gas sample, since mixing and diffusion of the gas sample in the chamber can be made sufficiently negligible. The gas flow rate for analysis differs significantly from the acquisition flow rate.

14 Claims, 7 Drawing Sheets

METHODS FOR RAPID GAS SAMPLING WITH HIGH HORIZONTAL SPATIAL RESOLUTION IN A MANNER SUITABLE FOR SUBSEQUENT CONSTITUENT GAS ANALYSIS

CROSS REFERENCE TO RELATED APPLICATIONS

This application claims the benefit of U.S. provisional patent application 61/630,770, filed on Dec. 15, 2011, entitled "Methods for rapid gas sampling with high horizontal spatial resolution in a manner suitable for subsequent constituent gas analysis", and hereby incorporated by reference in its entirety.

FIELD OF THE INVENTION

This invention relates to gas analysis.

BACKGROUND

Numerous approaches for gas handling in gas analysis systems have been investigated to date. One recent example is considered in U.S. Pat. No. 7,597,014 by Pieter Tans. In this work, a long thin tube is used to continuously acquire a gas sample. After the sample has been acquired, the stored gas in the tube can be analyzed. This analysis can provide a time history of the gas sample.

SUMMARY

We have found that the above-described gas handling approach can be significantly enhanced in several ways. More specifically, we have found that it can be beneficial to have the sample gas analysis flow rate differ significantly from the sample gas acquisition rate. This can be regarded as being analogous to a tape recorder where the playback speed differs significantly form the recording speed. Use of a slower analysis flow rate can be beneficial for time-consuming analyses, such as isotope ratio measurements. Use of a faster analysis flow rate can be beneficial for multiple-sample analysis. Another enhancement is to provide on-board triggering for sample gas acquisition. These enhancements can be practiced separately or in combination.

DETAILED DESCRIPTION

In the fields of atmospheric and environmental science, it is often interesting and important to sample and analyze the constituents of ambient atmospheric gas with high horizontal spatial resolution. Examples of these applications include but are not limited to:

1) Stable isotope analysis of an on- or near-road source of methane for the purpose of attributing the methane to a known source such as natural gas; and 2) Analysis of a plume downwind of a factory, landfill, or other facility to quantify the concentrations of long-lived greenhouse gases or potentially harmful constituents.

Because these atmospheric plumes are transient in nature, and can vary rapidly on a spatial scale of meters, it can be difficult or impossible to make the necessary gas measurements in the vehicle in real time. To facilitate these measurements without compromising spatial or temporal resolution, we introduce the concept of a sample loop (i.e., a gas sample storage chamber) in which a horizontal transect of the gaseous plume is stored for later analysis without substantial loss of spatial resolution. As indicated above, playback of the stored sample is at a significantly different flow rate than the acquisition flow rate.

Figure 1:
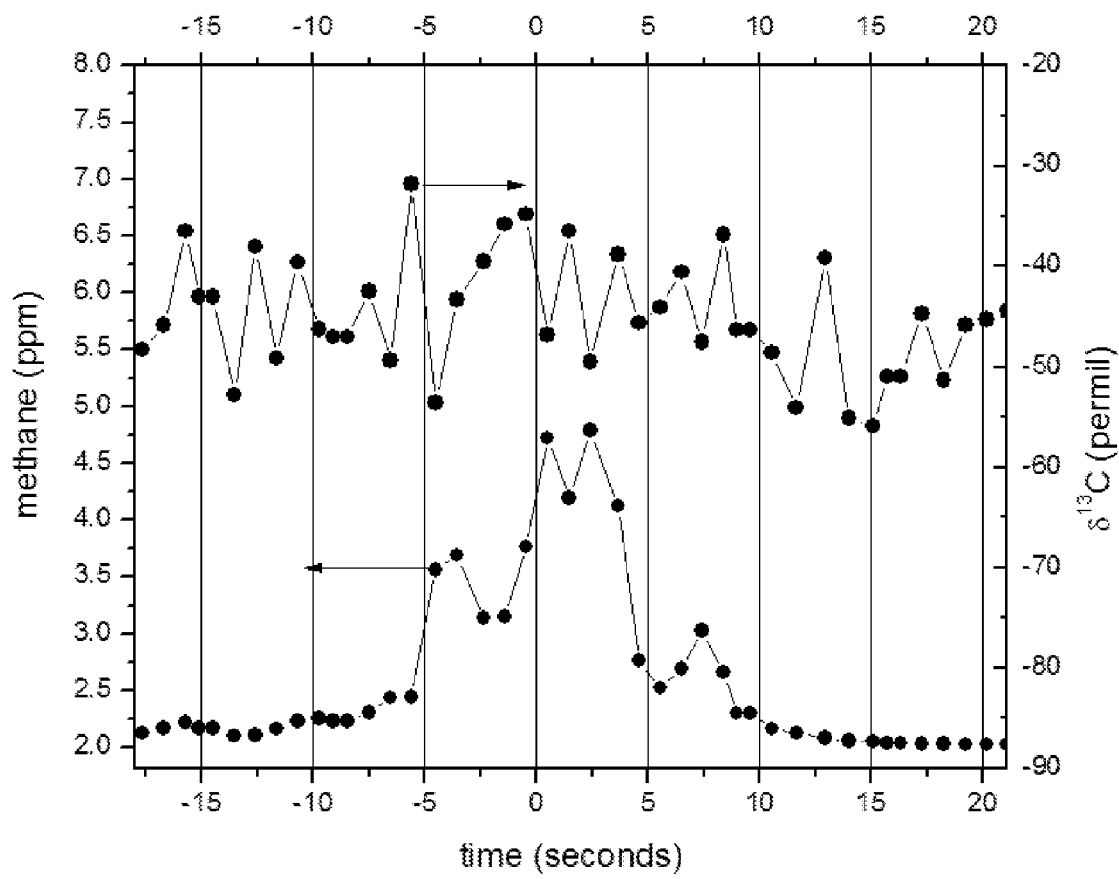
FIG. 1 shows a representative example of measured concentration and isotope ratio.
Figure 2:
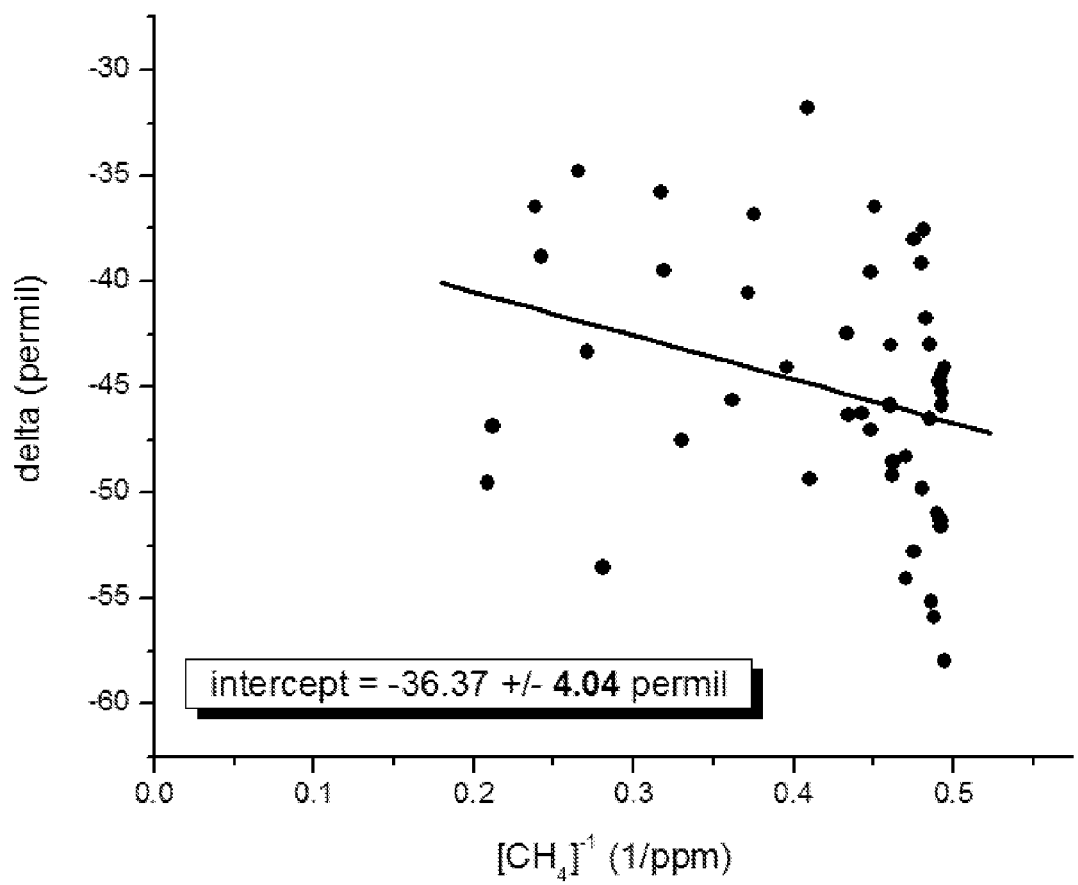
FIG. 2 is a Keeling plot of the results of FIG. 1.

FIG. 1 shows a representative example of measured concentration and isotope ratio from a conventional gas handling and measurement system. An important feature of this example is that the gas flow rate is relatively high, and as a result the data is undesirably limited. For example, the concentration peak seen on FIG. 1 includes roughly 10 data points, which can be fewer than what is desired. As a specific example, FIG. 2 is a Keeling plot of the results of FIG. 1. A Keeling plot is a plot of isotope ratio vs. 1/concentration, and it is apparent that the data set of FIG. 1 is sparse in the high concentration part of the Keeling plot (i.e., the left side of FIG. 2). As a result, the y-intercept uncertainty (which is the main quantity of interest on a Keeling plot) is undesirably increased. The y-intercept of a Keeling plot is of particular interest because it gives the estimated isotope ratio for the trace gas at 100% concentration (i.e., without any mixing from other gases).

Note that simply reducing the acquisition flow rate is frequently not an option. For example, if gas analysis is performed from a moving vehicle on ordinary roads, then the acquisition flow rate must be consistent with providing adequate horizontal sampling and resolution given typical vehicle speeds (e.g., 25 MPH to 45 MPH). Such considerations will dictate a minimum acquisition flow rate that will often be high enough to cause trouble in an isotope analysis, as in the example of FIGS. 1 and 2. Embodiments of the present invention can alleviate this problem.

Figure 3:
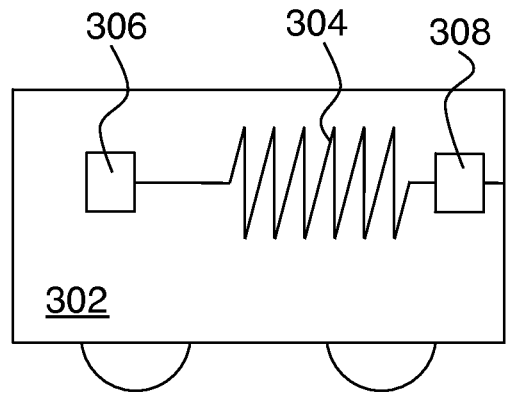
FIG. 3 shows a mobile platform including a gas sample storage chamber.

FIG. 3 shows a mobile platform including a gas sample storage chamber. More specifically, a mobile platform 302 includes a gas sample storage chamber 304, which can be arranged as a long coil of thin tubing as schematically shown. In such cases, the length to diameter ratio of the tube is preferably at least 100:1, more preferably at least 1000:1, and yet more preferably 5000:1 or more. Gas sample storage chamber 304 has a volume that is sufficient for subsequent gas analysis. More specifically, the minimum analysis volume for the analysis instrument(s) should be much smaller than the gas sample storage chamber volume, so that enough aliquots can be analyzed from a single sample to achieve the desired horizontal resolution spatially. Gas sample storage chamber 304 can have an inlet port and an outlet port for flowing gas through the chamber, or only an inlet port for injecting the analyte gas into the chamber.

Platform 302 can be any vehicle, such as a car, truck, van, unmanned aerial vehicle, or bicycle. Platform 302 can also be any other mobile entity capable of transporting the gas sample storage chamber, such as a person, pack animal, etc. Platform 302 is capable of moving over or near potential sources of gaseous emissions. An automobile on surface streets is a preferred mobile platform.

In order to provide recording and playback functions as considered herein, the gas sample storage container can have a linear configuration, and should have relatively low levels of mixing in the time span between gas sample acquisition and gas sample analysis. It is convenient to refer to this time span as the storage time. It would be highly undesirable for the gas sample to become spatially homogeneous via diffusion during the storage time.

A gas sample storage chamber configured as a long thin tube, as considered above, has been found suitable for providing the recording and playback functions. More specifically, one can define a diffusion length scale that is roughly the spatial spread due to diffusion for concentration gradients and storage times that arise in practice. Preferably, this diffusion length scale is less than about 20% of the tube length of the gas sample storage chamber. In general, the gas sample storage chamber has an aspect ratio that substantially prevents mixing of gas from one part of the volume to another during the storage time. Practically, this means a long thin tube or other container of similar aspect ratio.

Gas flow controllers 306 and 308 are disposed on platform 302 to control the flow of gas to or from the gas sample storage chamber. Practice of the invention does not depend on details of the gas flow controller construction or arrangement. Any gas flow controller arrangement capable of providing the acquisition and analysis modes as described herein is suitable. The gas flow arrangement may have valves and auxiliary tubing to direct the gas flow and a pump or alternative passive means of driving the flow. Preferably, ambient gas is admitted to the gas sample storage chamber at the acquisition flow rate under active control by a gas flow system (as opposed to passively admitting gas, e.g., in a gas flow driven by environmental pressure differences). Together with the gas sample storage chamber, the system can have up to four basic operational states: 1) sample injection state (acquisition mode), 2) sample storage state, 3) sample analysis state (analysis mode), and 4) sample purge or evacuation state.

A gas inlet system can be located externally on the platform. One implementation is to place this inlet on the roof (of a vehicular platform). A second implementation is to place this inlet at the front of the platform as close to ground level as is practical, with one or more discrete inlet ports (or a diffusive inlet) that span the width of the platform. Practice of the invention does not depend critically on details of the gas inlet(s).

Optionally, a mixing volume can be added to the flow control system to smooth out very fast changes in the concentration without substantially reducing the ultimate horizontal spatial resolution that can be achieved with the system.

Optionally, a sample conditioning device (such as a particulate filter or chemical scrubber) can be included to remove one or more components of the sampled air to increase the storage time or remove potential cross-talk with other species (such as water vapor).

Figure 4A:
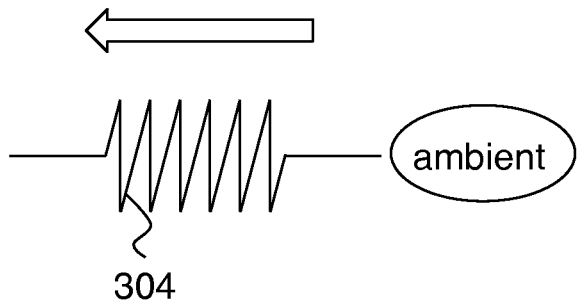
FIGS. 4a-c show several operating modes according to embodiments of the invention.
Figure 4B:
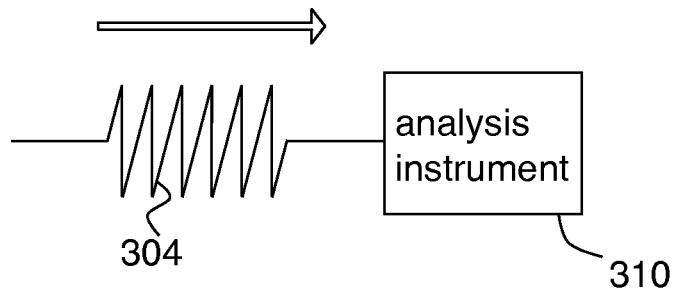
Figure 4C:
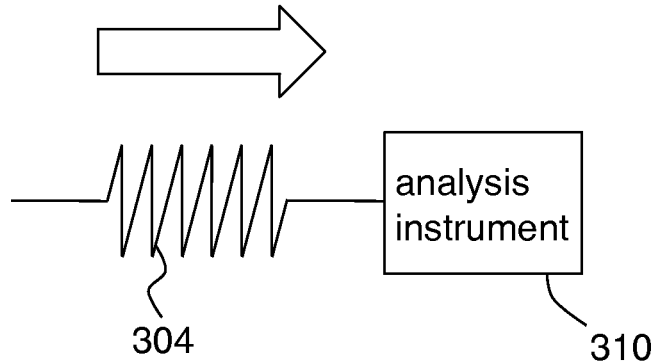

FIGS. 4a-c show several operating modes according to embodiments of the invention. FIG. 4a shows an acquisition mode, where gas from an ambient flows into gas sample storage chamber 304 at an acquisition flow rate (schematically shown with an outline arrow). During acquisition, the platform should move directly over the source of gas or downwind of the source in a manner that intercepts the downwind plume.

FIG. 4b shows an analysis mode, where gas from the gas sample storage chamber 304 flows to a gas analysis instrument 310 at an analysis flow rate (schematically shown with an outline arrow). In the example of FIG. 4b, this analysis flow rate is substantially less than the acquisition flow rate (schematically shown with a narrower outline arrow than on FIG. 4a). This configuration is especially useful for when the analysis method is very slow, such as isotope analysis or gas chromatography.

FIG. 4c also shows an analysis mode, where gas from the gas sample storage chamber 304 flows to a gas analysis instrument 310 at the analysis flow rate (schematically shown with an outline arrow). In the example of FIG. 4c, this analysis flow rate is substantially greater than the acquisition flow rate (schematically shown with a wider outline arrow than on FIG. 4a). This configuration can enable the analysis of multiple gas sample storage chambers in a short period of time.

Thus, a method according to an embodiment of the invention includes providing a mobile platform and providing a gas sample storage chamber disposed on the mobile platform. The gas sample storage chamber has at least an acquisition mode and an analysis mode. In the acquisition mode, sample gas is acquired from at least two distinct locations as the mobile platform moves by continuously admitting ambient gas to the gas sample storage chamber at an acquisition flow rate. In the analysis mode, sample gas flows from the gas sample storage chamber to a gas analysis instrument at an analysis flow rate. The acquisition flow rate and the analysis flow rate differ by 40% or more of the acquisition flow rate.

The analysis flow rate can be faster or slower than the acquisition flow rate. For example, a suitable acquisition flow rate for isotope analysis can be from 500 sccm to 20,000 sccm (standard cubic centimeters/minute), and the corresponding analysis flow rate can be less than 0.5× the acquisition flow rate (e.g., from 0.01× to 0.5× the acquisition flow rate). For multiple-sample analysis, a suitable acquisition flow rate can be from 25 sccm to 500 sccm, and the corresponding analysis flow rate can be greater than 2× the acquisition flow rate (e.g., from 2× to 10× the acquisition flow rate).

In preferred embodiments of the invention, gas measurements are related to position of the mobile platform. For example, position vs. time measurements of the mobile platform can be combined with gas measurements vs. time to provide gas measurements vs. position. A measurement rate of about 1 position measurement per second has been found to suffice in practice. The Global Positioning System (GPS) is suitable for providing platform position vs. time measurements, but any other approach for providing such data can also be employed.

Optionally, the diffusion of the gas within the gas sample storage chamber can be modeled so that a truer representation of the horizontal gas profile can be achieved. Also optionally, other aspects of the response of the system (e.g., surface adhesion) can be modeled so that a truer representation of the horizontal gas profile can be achieved.

Figure 5:
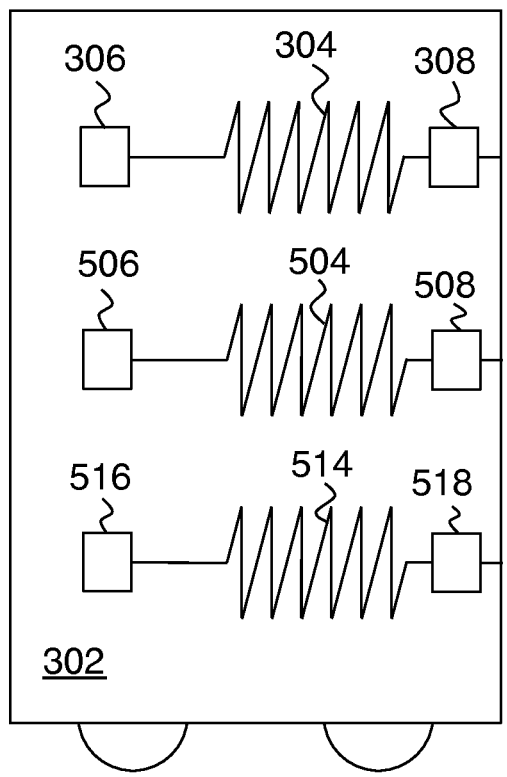
FIG. 5 shows an example of several gas sample storage chambers on a mobile platform.

In some cases, several gas sample storage chambers can be included on the same mobile platform. FIG. 5 shows an example. Here platform 302 includes auxiliary gas sample storage chambers 504 and 514. Gas flow to/from chamber 504 is controlled by controllers 506 and 508. Similarly, gas flow to/from chamber 514 is controlled by controllers 516 and 518. Operation of the auxiliary chambers is similar to the operation of chamber 304 as described above. For each chamber, there is an acquisition flow rate and an analysis flow rate, where the analysis flow rate differs from the acquisition flow rate by 40% or more. The flow rates for different chambers can be the same or different. With this approach, more than one gas sample storage chamber can be used to generate multiple horizontal transects simultaneously.

Figure 6A:
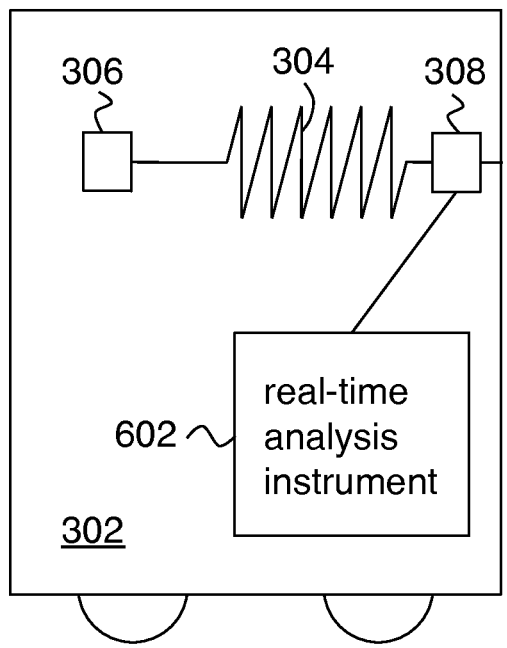
FIGS. 6a-b show exemplary configurations including an on-board real-time analysis instrument.
Figure 6B:
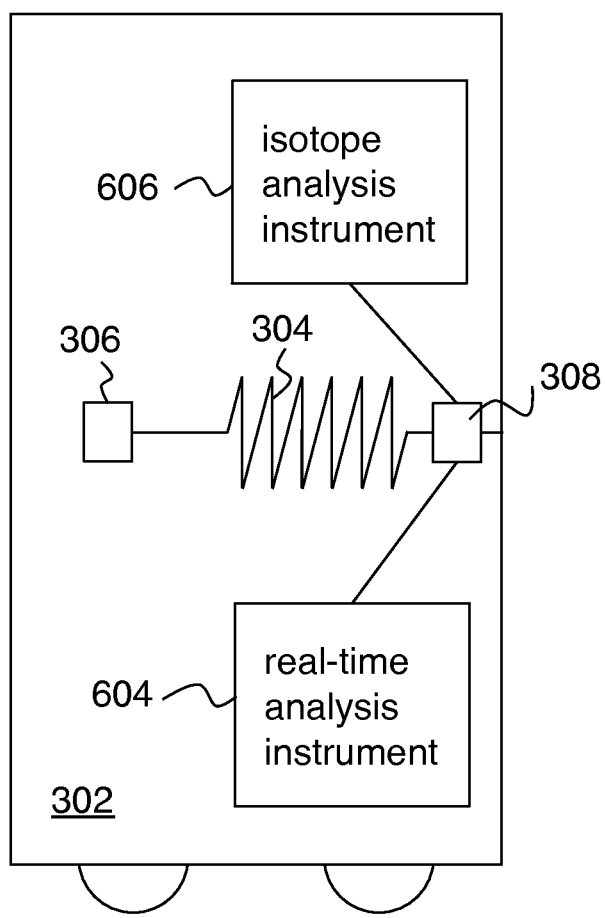

In some cases, it is beneficial to include a real-time analysis instrument on the mobile platform. FIGS. 6a-b show two examples. In the example of FIG. 6a, a real-time analysis instrument 602 is included on platform 302. Such a configuration can be operated in various ways. For example, instrument 602 can be used to switch the system from an idle mode to the acquisition mode depending on measured readings. Instrument 602 can also be used to switch the system from the acquisition mode to the analysis mode depending on measured readings. In other words, the real-time instrument 602 can provide a trigger for switching the mode of the system.

The operational state (acquiring, storing, analyzing, or purging) of the gas sample storage chamber and flow control system can be triggered either manually (e.g., by user input) or automatically, based on some combination of indicators. The following list is a representative but not exhaustive list of such indicators:

1) Geospatial information (e.g., latitude, longitude, or physical landmarks);
2) Meteorological information (e.g., wind speed, wind direction, atmospheric stability);
3) Time; and
4) Real-time gas analysis of the inlet air (e.g., trace gas concentrations or isotopes).

Practice of the invention does not depend critically on the location of the gas analysis instrument (or instruments). The gas analysis instrument(s) can be located on the mobile platform (i.e., on-board) or off the mobile platform (as implicitly shown on FIGS. 4b-c). In cases where the gas analysis instrument is disposed on-board, two cases can be considered. The first case, shown on FIG. 6a, relates to a single instrument 602 that is capable of providing the trigger input for switching the operating mode, and is also capable of performing the playback analysis. The second case, shown on FIG. 6b, relates to two instruments, 604 and 606, where 604 is a real time instrument that provides the trigger input for switching the operating mode, and 606 is the instrument used for performing the playback analysis.

Further variations on the basic idea of controlling system operation according to on-board measurements are possible. For example, the analysis flow rate can depend in part on a measured gas analysis signal obtained during the analysis mode from the gas analysis instrument. More specifically, the analysis flow rate can be automatically decreased if the gas analysis signal decreases, in order to automatically attempt to improve signal to noise ratio.

Figure 7:
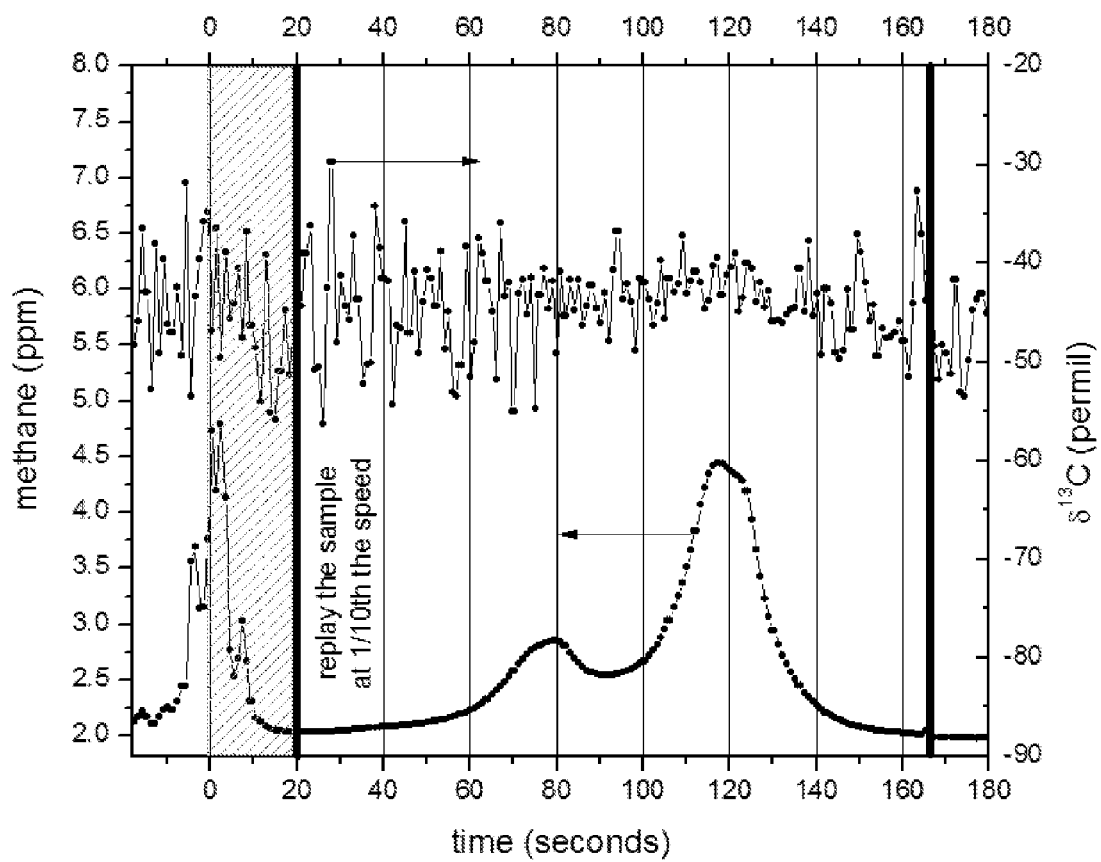
FIG. 7 shows an example of measured concentration and isotope ratio using reduced flow rate playback from the gas sample storage chamber.
Figure 8:
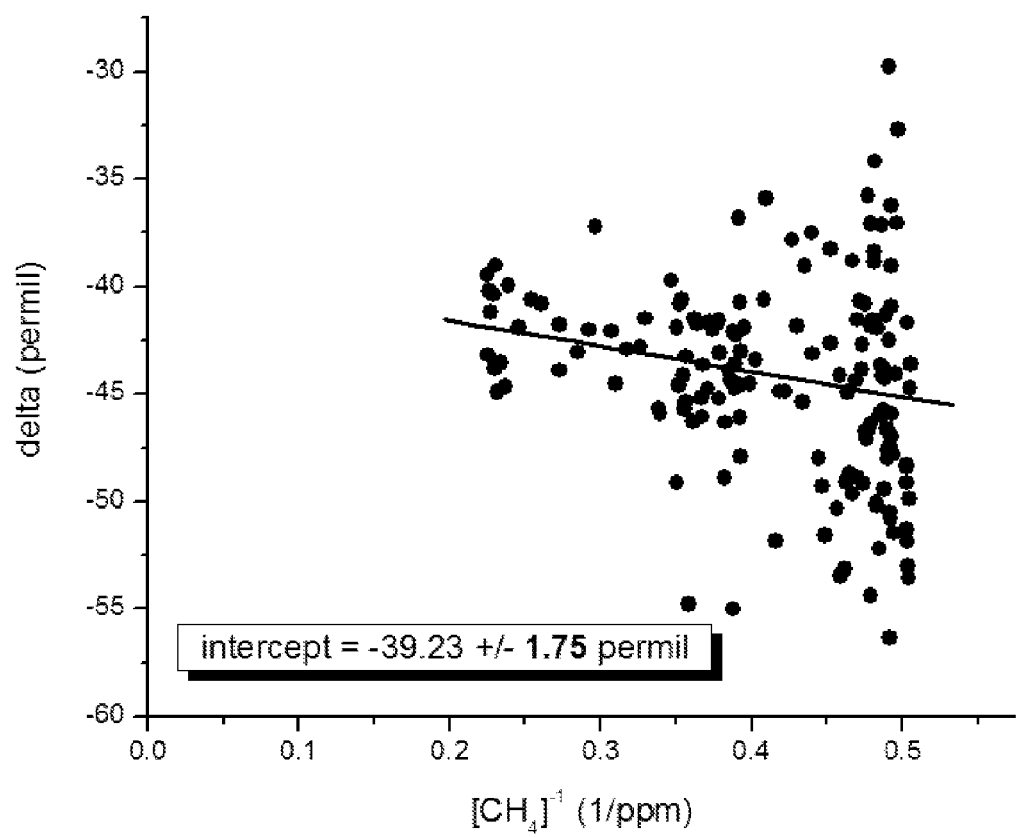
FIG. 8 is a Keeling plot of the results of FIG. 7.

FIG. 7 shows an example of measured concentration and isotope ratio using reduced flow rate playback from the gas sample storage chamber. More specifically, the sample is played back at 1/10 the flow rate (and in reverse), as can be seen from the figure. By comparing this data to the data of FIG. 1, it is apparent that there are far more data points in the measured concentration peak. The corresponding Keeling plot of FIG. 8 shows more high-concentration data (on the left side of the plot), and a reduced y-intercept uncertainty (about a 2.4× improvement in this example).

The preceding description has been by way of example as opposed to limitation, and numerous variations of the given examples also amount to practicing embodiments of the invention. For example, the given examples all show playback in reverse, where the same end of the gas sample storage chamber is use to admit gas in acquisition mode and to provide gas in analysis mode. Forward playback, where opposite ends of the gas sample storage chamber are used to admit gas in acquisition mode and to provide gas in analysis mode, is also possible.

The invention claimed is:

1. A method of gas analysis, the method comprising:
providing a mobile platform;
providing a gas sample storage chamber disposed on the mobile platform and configured to have an acquisition mode where sample gas is acquired from at least two distinct locations as the mobile platform moves by continuously admitting ambient gas to the gas sample storage chamber at an acquisition flow rate;
performing analysis of the sample gas by flowing the sample gas from the gas sample storage chamber to a gas analysis instrument in an analysis mode and at an analysis flow rate, wherein the acquisition flow rate and the analysis flow rate differ by 40% or more of the acquisition flow rate;
wherein switching from the acquisition mode to the analysis mode is based on a trigger.

2. The method of claim 1, wherein the analysis flow rate is slower than the acquisition flow rate.

3. The method of claim 2, wherein the analysis flow rate is between 0.01 and 0.5 times the acquisition flow rate.

4. The method of claim 2, wherein the gas analysis instrument is an isotope ratio instrument.

5. The method of claim 1, wherein the analysis flow rate is faster than the acquisition flow rate.

6. The method of claim 5, wherein the analysis flow rate is 2 or more times the acquisition flow rate.

7. The method of claim 5, further comprising:
providing one or more auxiliary gas sample storage chambers disposed on the mobile platform and configured to have an acquisition mode where sample gas is acquired from at least two distinct locations as the mobile platform moves by continuously admitting ambient gas to the auxiliary gas sample storage chambers at an auxiliary acquisition flow rate;
performing analysis of the sample gas by flowing the sample gas from the auxiliary gas sample storage chambers to the gas analysis instrument at an auxiliary analysis flow rate, wherein the auxiliary acquisition flow rate and the auxiliary analysis flow rate differ by 40% or more of the auxiliary acquisition flow rate.

8. The method of claim 1, wherein the trigger is provided by a real-time gas analysis instrument disposed on the mobile platform.

9. The method of claim 1, wherein the trigger is provided by the gas analysis instrument, and wherein the gas analysis instrument is a real-time instrument disposed on the mobile platform.

10. The method of claim 1, wherein the trigger is provided by an indicator selected from the group consisting of: physical landmarks, latitude and longitude data, wind speed, wind direction, atmospheric stability, time, and user input.

11. The method of claim 1, wherein the gas sample storage chamber is configured as a tube having a length to diameter ratio of 100 or more.

12. The method of claim 1, further comprising:
performing position vs. time measurements of the mobile platform; and
relating the position vs. time measurements of the mobile platform to gas measurements vs. time to provide gas measurements vs. position.

13. The method of claim 1, wherein the analysis flow rate depends in part on a measured gas analysis signal obtained during the analysis mode from the gas analysis instrument.

14. The method of claim 1, wherein ambient gas is admitted to the gas sample storage chamber at the acquisition flow rate under active control by a gas flow system.

* * * * *